United States Patent [19]
Takeo et al.

[11] Patent Number: 5,714,764
[45] Date of Patent: Feb. 3, 1998

[54] METHOD FOR DETECTING PROSPECTIVE ABNORMAL PATTERNS

[75] Inventors: Hideya Takeo; Nobuyoshi Nakajima, both of Kanagawa-ken, Japan

[73] Assignee: Fuji Photo Film Co., Ltd., Kanagawa, Japan

[21] Appl. No.: 730,024

[22] Filed: Oct. 11, 1996

[30] Foreign Application Priority Data

Oct. 12, 1995 [JP] Japan .................... 7-264021

[51] Int. Cl.$^6$ .................... G01N 23/04
[52] U.S. Cl. .................... 250/587; 378/37
[58] Field of Search .................... 378/37; 250/584, 250/587

[56] References Cited

U.S. PATENT DOCUMENTS

| | | | |
|---|---|---|---|
| 4,527,060 | 7/1985 | Suzuki et al. | 250/327.2 |
| 5,046,147 | 9/1991 | Funahashi et al. | 205/327.2 |
| 5,583,346 | 12/1996 | Nakajima | 250/587 |

OTHER PUBLICATIONS

"Detection of Tumor Patterns in DR Images (Iris Filter)," Obata, et al., Collected Papers of The Institute of Electronics and Communication Engineers of Japan, D-II, J75-D-II, No. 3, pp. 663-670, Mar. 1992.

"Extraction of Small Calcified Patterns with a Morphology Filter Using a Multiply Structure Element," Collected Papers of The Institute of Electronics and Communication Engineers of Japan, D-II, vol. J75-D-II, No. 7, pp. 1170-1176, Jul. 1992.

"Fundamentals of Morphology and Its Application to Mammogram Processing," Medical Imaging Technology, vol. 12, No. 1, Jan. 1994.

*Primary Examiner*—David P. Porta
*Assistant Examiner*—David Vernon Bruce
*Attorney, Agent, or Firm*—Sughrue, Mion, Zinn, Macpeak & Seas, PLLC

[57] ABSTRACT

A stimulable phosphor sheet, on which a radiation image of an object has been stored, is exposed to stimulating rays, which cause the stimulable phosphor sheet to emit light in proportion to the amount of energy stored thereon during its exposure to radiation. The emitted light is detected by a photoelectric read-out device, and an image signal representing the radiation image is thereby obtained. Threshold value processing is carried out in accordance with the obtained image signal, and a prospective abnormal pattern is thereby detected from the radiation image. A predetermined threshold value, which is used in the threshold value processing for detecting the prospective abnormal pattern, is set to be a small value as the amount of change in the image signal corresponding to the region in the vicinity of the prospective abnormal pattern becomes large.

30 Claims, 9 Drawing Sheets

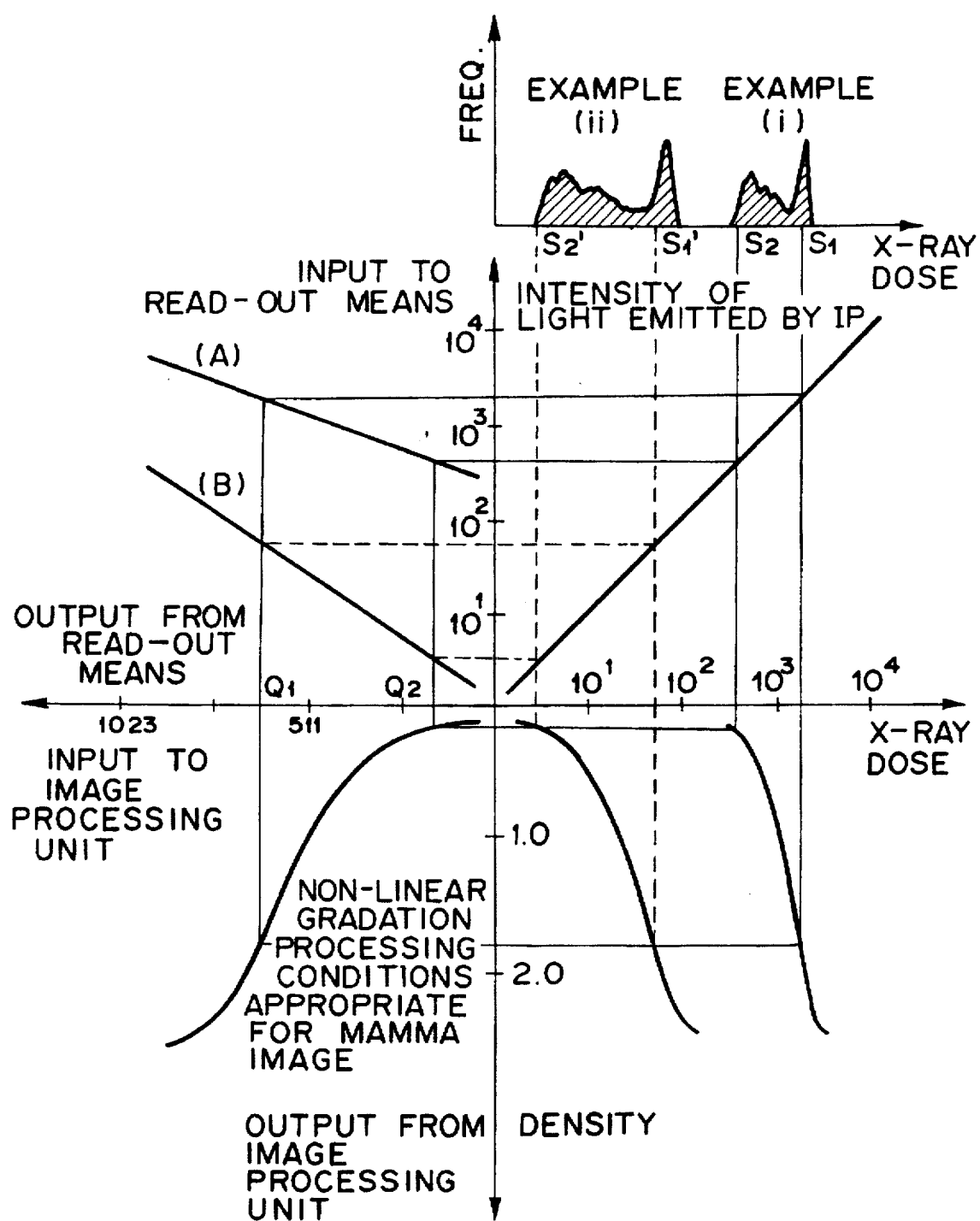

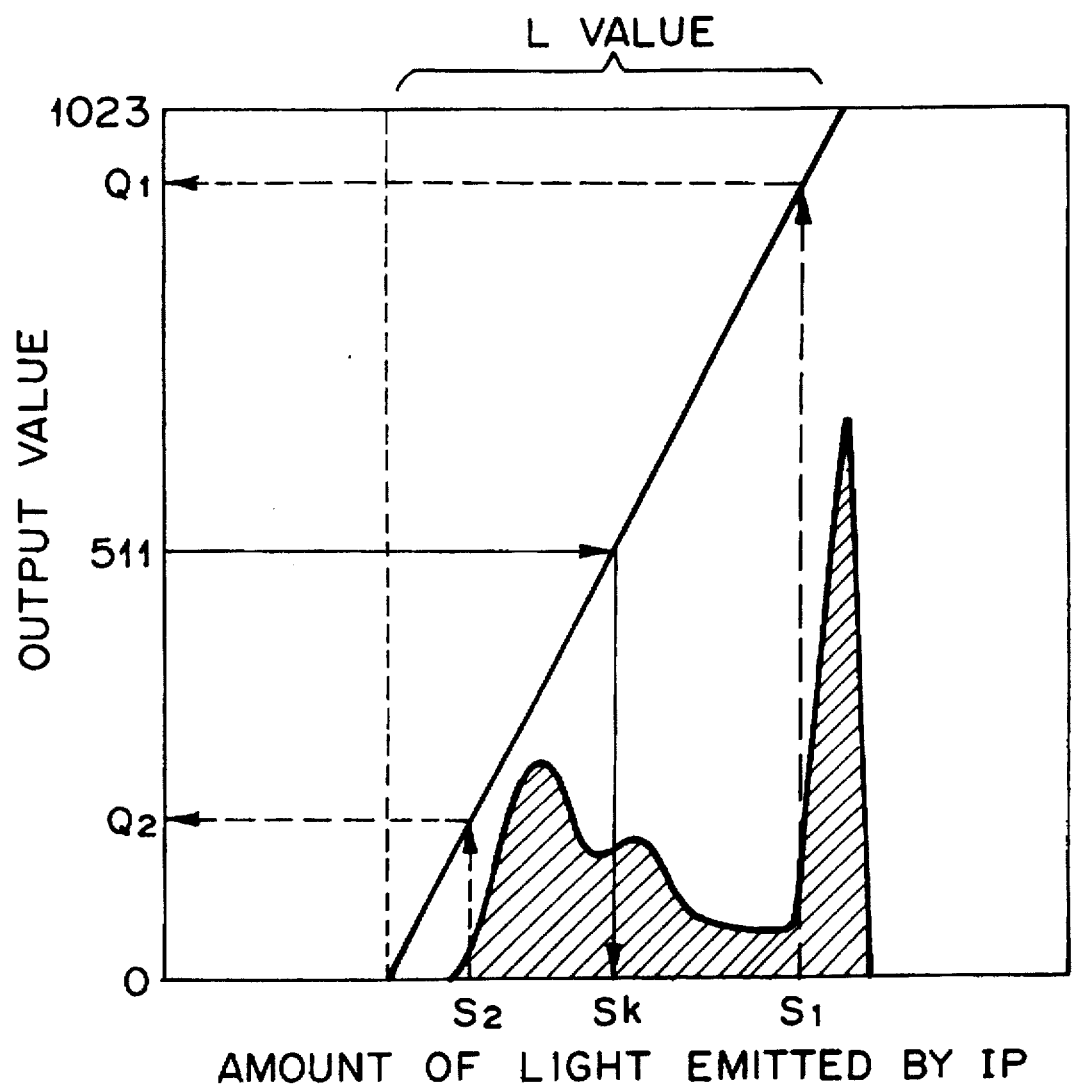

METHOD FOR DETECTING PROSPECTIVE ABNORMAL PATTERNS

BACKGROUND OF THE INVENTION

1. Field of the Invention

This invention relates to a method for detecting a prospective abnormal pattern from an image.

2. Description of the Prior Art

Techniques for reading out a radiation image of an object and reproducing a visible radiation image have heretofore been carried out in various fields. With the techniques, a radiation image of an object, which has been recorded on a recording medium, such as a stimulable phosphor sheet or X-ray film, is read out, an image signal is thereby obtained, and the obtained image signal is subjected to appropriate image processing and then used for reproducing a visible image on a display device, or the like. In particular, recently, various digital radiography techniques, which utilize computers and are referred to as computed radiography (CR), have been proposed and applied to clinical diagnoses, or the like.

In cases where a stimulable phosphor sheet is employed as the recording medium, the radiation image of an object is stored as a level of energy during the exposure of the stimulable phosphor sheet to radiation. In such cases, the image signal representing the radiation image is obtained by exposing the stimulable phosphor sheet to stimulating rays, which cause it to emit light in proportion to the amount of energy stored thereon during its exposure to radiation, and detecting the emitted light with a photoelectric read-out means.

In the CR, a read-out sensitivity and contrast adjusting function, which is referred to as the exposure data recognizer (EDR), is employed. With the EDR, a preliminary read-out operation (hereinbelow referred to as the "preliminary readout") is carried out in order to approximately ascertain the image information of a radiation image, which has been stored on a stimulable phosphor sheet. An electric image signal, which is to be used in reproducing a visible image capable of being used for diagnostic purposes, or the like, is obtained from a final read-out operation (hereinbelow referred to as the "final readout"). During the preliminary readout, stimulating rays are used, which have an energy level lower than the energy level of the stimulating rays used in the final readout. In accordance with the image information having been obtained from the preliminary readout, read-out conditions for the final readout, such as a read-out sensitivity (hereinbelow often referred to as the S value) and a latitude (hereinbelow often referred to as the L value), are adjusted such that the visible image reproduced from the image signal, which is obtained from the final readout, can have good image quality, e.g. an appropriate density and an appropriate contrast, and can serve as an effective tool in, particularly, the efficient and accurate diagnosis of an illness.

A method for utilizing the preliminary readout and the final readout has been disclosed in, for example, U.S. Pat. No. 4,527,060. With the disclosed method, the final readout is carried out under the read-out conditions, which have been adjusted with the EDR. The image signal obtained from the final readout is fed into an image processing means. In the image processing means, the image signal is processed in accordance with the portion of the object the image of which is recorded, the conditions under which the image is recorded, or the like, such that a visible image suitable for the diagnostic purposes, or the like, can be reproduced. A visible image is then reproduced from the processed image signal on a photographic material, or the like.

Also, a processing method, wherein the preliminary readout need not be carried out, time loss due to the preliminary readout is thereby eliminated, and the processing and the apparatus are thereby kept simple, has been proposed in, for example, U.S. Pat. No. 5,046,147. With the proposed processing method, the detection range for the light emitted by a stimulable phosphor sheet is set to be sufficiently wide (for example, approximately 4 orders of ten), and the entire radiation image is thereby read out to obtain an image signal. From the obtained image signal, an appropriate read-out sensitivity and an appropriate latitude are determined. Thereafter, in accordance with the determined read-out sensitivity and the determined latitude, the obtained image signal is transformed into an image signal, which is equivalent to the image signal, which would be obtained if the image were again read out under the conditions of the determined read-out sensitivity and the determined latitude.

With the proposed processing method, the setting values of the photoelectric read-out means with respect to the amount of the stimulating rays irradiated to the stimulable phosphor sheet, the sensitivity, the dynamic range, and the like, need not be set again, and an image signal necessary to reproduce an appropriate image can be obtained.

Further, particularly for medical diagnoses of human bodies, techniques referred to as the computer aided diagnosis of medical images (CADM) have been proposed, which aim at more positively utilizing the features of the digital radiography.

The techniques for the computer aided diagnosis of medical images, or the like, assist in making diagnoses by reading patterns in an image at the sites of medical treatment. Specifically, in the past, medical specialists visually read patterns in radiation images having been reproduced on recording media, such as X-ray film, display devices, such as cathode ray tube (CRT) display devices, or the like, and made efforts in order to find out abnormal tumor patterns, which represented cancers, or the like, small calcified patterns, which are smaller than the tumor patterns and have a density lower than the density of them, and the like, in the early stages of the diseases. (The tumor patterns, the small calcified patterns, and the like, will hereinbelow be referred to as the abnormal patterns.) However, in such cases, there is the risk that the abnormal patterns are left unnoticed or are misunderstood due to subjective judgments, depending on differences between the image understanding capabilities of persons, who view the radiation images.

Therefore, the techniques for the computer aided diagnosis of medical images aim at preventing the persons, who view the radiation images, from failing to notice the abnormal patterns and misunderstanding the abnormal patterns, and thereby aim at enabling the persons to make the efficient and accurate diagnosis of an illness. For such purposes, with the techniques for computer aided diagnosis of medical images, a prospective abnormal pattern, which is considered as being an abnormal pattern, is detected. Also, a marking is put on the detected portion in order to arouse an attention of the person, who views the radiation image. Alternatively, characteristics of the detected prospective abnormal pattern are indicated quantitatively as materials, which are useful for objective judgments of the person, who views the radiation image. [Reference should be made to "Detection of Tumor Patterns in DR Images (Iris Filter)," Collected Papers of The Institute of Electronics and Communication Engineers of Japan, D-II, Vol. J75-D-II, No. 3, pp. 663–670, March 1992;

and "Extraction of Small Calcified Patterns with A Morphology Filter Using A Multiply Structure Element," Collected Papers of The Institute of Electronics and Communication Engineers of Japan, D-II, Vol. J75-D-II, No. 7, pp. 1170–1176, July 1992.]

How the morphology processing is carried out will be described hereinbelow. The morphology processing is the technique for detecting a small calcified pattern, which is one of the characteristic forms of mammary cancers as in the cases of the tumor patterns. The morphology processing is carried out by using a multi-scale λ and a structure element (i.e., a mask) B. The morphology processing has the features in that, for example, (1) it is efficient for extracting a calcified pattern itself, (2) it is not affected by complicated background information, and (3) the extracted calcified pattern does not become distorted. Specifically, the morphology processing is advantageous over ordinary differentiation processing in that it can more accurately detect the geometrical information concerning the size, the shape, and the density distribution of the calcified pattern. The morphology processing is carried out in the manner described below. (Fundamental operation of morphology processing)

In general, the morphology operation is expanded as the theory of sets in an N-dimensional space. As an aid in facilitating the intuitive understanding, the morphology operation will be described hereinbelow with reference to a two-dimensional gray level image.

The gray level image is considered as a space, in which a point having coordinates (x, y) has a height corresponding to a density value f(x, y). In this case, it is assumed that the image signal representing the density value f(x, y) is a high luminance-high signal level type of image signal, in which a low density (i.e., a high luminance when the image is displayed on a CRT display device) is represented by a high image signal level.

Firstly, as an aid in facilitating the explanation, a one-dimensional function f(x) corresponding to the cross-section of the space is considered. It is assumed that structure element g used in the morphology operation is a symmetric function of Formula (1), which is symmetric with respect to the origin.

$$g^s(x) = g(-x) \quad (1)$$

It is also assumed that the value is 0 in a domain of definition G, which is represented by Formula (2).

$$G = \{-m, -m+1, \ldots, -1, 0, 1 \ldots m\} \quad (2)$$

In such cases, the fundamental forms of the morphology operation are very simple operations carried out with Formulas (3), (4), (5) and (6).

$$\begin{aligned}
&\text{dilation: } [f \oplus G^s](i) = \max\{f(i-m), \ldots, f(i), \ldots, f(i+m)\} &(3)\\
&\text{erosion: } [f \ominus G^s](i) = \min\{f(i-m), \ldots, f(i), \ldots, f(i+m)\} &(4)\\
&\text{opening: } f^s = (f \ominus g^s) \oplus g &(5)\\
&\text{closing: } f^s = (f \oplus g^s) \ominus g &(6)
\end{aligned}$$

Specifically, as illustrated in FIG. 5A, the dilation processing is the processing for retrieving the maximum value in a width of ±m (the value determined in accordance with a structure element B) having its center at a picture element of interest. As illustrated in FIG. 5B, the erosion processing is the processing for retrieving the minimum value in the width of ±m having its center at the picture element of interest. The opening processing is equivalent to the searching of the maximum value after the searching of the minimum value. Also, the closing processing is equivalent to the searching of the minimum value after the searching of the maximum value. More specifically, as illustrated in FIG. 5C, the opening processing is equivalent to the processing for smoothing the density curve f(x) from the low luminance side, and removing a convex density fluctuating portion (i.e., the portion at which the luminance is higher than that of the surrounding portions), which fluctuates in a range spatially narrower than the mask size of 2m. Also, as illustrated in FIG. 5D, the closing processing is equivalent to the processing for smoothing the density curve f(x) from the high luminance side, and removing a concave density fluctuating portion (i.e., the portion at which the luminance is lower than that of the surrounding portions), which fluctuates in the range spatially narrower than the mask size of 2m.

In cases where the structure element g is not symmetric with respect to the origin, the dilation operation with Formula (3) is referred to as the Minkowski sum, and the erosion operation with Formula (4) is referred to as the Minkowski difference.

In cases where the image signal representing the density value f(x) is a high density-high signal level type of image signal, in which a high density is represented by a high image signal level, the relationship between the density value f(x) and the image signal value becomes reverse to the relationship between the density value f(x) and the image signal value in the high luminance-high image signal level type of image signal. Therefore, the dilation processing, which is carried out on the high density-high signal level type of image signal, coincides with the erosion processing, which is carried out on the high luminance-high signal level type of image signal as shown in FIG. 5B. The erosion processing, which is carried out on the high density-high signal level type of image signal, coincides with the dilation processing, which is carried out on the high luminance-high signal level type of image signal as shown in FIG. 5A. The opening processing, which is carried out on the high density-high signal level type of image signal, coincides with the closing processing, which is carried out on the high luminance-high signal level type of image signal as shown in FIG. 5D. Also, the closing processing, which is carried out on the high density-high signal level type of image signal, coincides with the opening processing, which is carried out on the high luminance-high signal level type of image signal as shown in FIG. 5C.

The morphology processing is herein described with respect to the high luminance-high signal level type of image signal (i.e., the image signal representing the luminance value).

(Application to detection of calcified patterns)

In order for a calcified pattern to be detected, it is considered to employ a difference method, in which a smoothed image signal is subtracted from the original image signal. However, with a simple smoothing method, it is difficult to discriminate the calcified pattern from an elongated non-calcified pattern (for example, a pattern of the mammary gland, a blood vessel, mammary gland supporting tissues, or the like). Therefore, Obata of Tokyo University of Agriculture and Technology, et al. have proposed a morphology filter, which is represented by Formula (7) and is based upon the opening operation using a multiply structure element. [Reference should be made to "Extraction of Small Calcified Patterns with A Morphology Filter Using A Multiply Structure Element," Collected Papers of The Institute of Electronics and Communication Engineers of Japan, D-II, Vol. J75-D-II, No. 7, pp. 1170–1176, July 1992; and "Fundamentals of Morphology and Its Application to Mammogram Processing," Medical Imaging Technology, Vol. 12, No. 1, January 1994.]

$$P = f - \max_{i \in (1,\ldots,M)} \{(f \ominus Bi) \oplus Bi\} \quad (7)$$

$$= f - \max_{i \in (1,\ldots,M)} \{f_{Bi}\}$$

In Formula (7), Bi (wherein i=1, 2 ..., M) represents, for example, four linear structure elements B (in this case, M=4) shown in FIG. 6. (The four structure elements, as a whole, will hereinbelow be referred to as the multiply structure element.) In cases where the structure element B is set to be larger than the calcified pattern to be detected, a calcified pattern, which is a convex signal change portion finer than the structure element B (i.e., which is an image portion fluctuating in a spatially narrow range), is removed in the opening processing. On the other hand, an elongated non-calcified pattern is longer than the structure element B. Therefore, in cases where the inclination of the non-calcified pattern (i.e., the direction along which the non-calcified pattern extends) coincides with one of the directions of the four structure elements Bi, the non-calcified pattern remains unremoved after the opening processing, i.e. the operation of the second term of Formula (7), has been carried out. Therefore, when the smoothed image signal obtained from the opening processing (i.e. the signal representing the image, from which the calcified pattern has been removed) is subtracted from the original image signal f, an image can be obtained which contains only the small prospective calcified pattern. This is the concept behind Formula (7).

As described above, in cases where the image signal is of the high density-high signal level type, the density value of the calcified pattern is smaller than the density values of the surrounding image portions, and the calcified pattern constitutes a concave signal change portion with respect to the surrounding portions. Therefore, the closing processing is applied in lieu of the opening processing, and Formula (8) is applied in lieu of Formula (7).

$$P = f - \min_{i \in (1,\ldots,M)} \{(f \oplus Bi) \ominus Bi\} \quad (8)$$

$$= f - \min_{i \in (1,\ldots,M)} \{f_{Bi}\}$$

However, it often occurs that a non-calcified pattern having the same size as the size of the calcified pattern remains in the obtained image. In such cases, the signal, which represents the non-calcified pattern and is contained in P of Formula (7), is removed by utilizing the differentiation information based upon the morphology operation carried out with Formula (9).

$$M_{grad} = (\tfrac{1}{2}) \times \{f \oplus \lambda B - f \ominus \lambda B\} \quad (9)$$

A large value of Mgrad indicates a high possibility of being a calcified pattern. Therefore, a prospective calcified pattern Cs can be detected with Formula (10).

IF $P(i,j) \geq T1$ and $M_{grad}(i,j) \geq T2$

Then $C_s(i,j)=P$ else $C_s(i,j)=0$ \quad (10)

In Formula (10), T1 and T2 represents the predetermined threshold values, which can be determined experimentally.

However, a non-calcified pattern, which has a size different from the size of the calcified pattern, can be removed by only the comparison of P of Formula (7) and the predetermined threshold value T1. Therefore, in cases where there is no risk that a non-calcified pattern having the same size as the size of the calcified pattern remains, it is sufficient for the condition of the first term of Formula (10), i.e. the condition of $P(i, j) \geq T1$, to be satisfied.

Finally, the cluster Cc of the calcified pattern is detected by the combination of the opening operation and the closing operation of the multi-scale in accordance with Formula (11).

$$C_c = C_s \oplus \lambda_1 B \ominus \lambda_3 B \oplus \lambda_2 B \quad (11)$$

In Formula (11), $\lambda_1$ and $\lambda_2$ are respectively determined by the maximum distance of the calcified pattern to be combined and the maximum radius of the isolated pattern to be removed, and $\lambda_3 = \lambda_1 + \lambda_2$.

As for the high luminance-high signal level type of image signal, the morphology filter is operated in the manner described above. In cases where the image signal is of the high density-high signal level type (in which a picture element of a high density has a large digital signal value), the relationship between the opening operation and the closing operation is reversed.

The threshold values T1 and T2, which are used in the morphology filter processing in order to make a judgment as to whether the pattern is or is not the prospective abnormal pattern, are the fixed values having been set experimentally. On the other hand, as described above, the image signal, which is subjected to the processing for detecting the prospective abnormal pattern, is composed of signal values obtained with the read-out sensitivity and the latitude having been adjusted by the EDR.

Therefore, the signal values also contain quantum noise of the radiation which are contained in the radiation image. The level of the image signal representing the quantum noise component fluctuates in accordance with the adjustment of the read-out sensitivity and the latitude carried out by the EDR.

As described above, the level of the image signal representing the quantum noise component fluctuates in accordance with the EDR. In such cases, if the threshold value, which is used in making a judgment as to whether the pattern is or is not the prospective abnormal pattern, is kept constant, there is the risk that the image signal representing the quantum noise component is detected by mistake as the one representing the prospective abnormal pattern.

In view of the above circumstances, a novel method for detecting a prospective abnormal pattern has been proposed, wherein the level of a threshold value is set appropriately in accordance with the read-out sensitivity and/or the latitude having been obtained with the EDR, and the accuracy, with which a prospective abnormal pattern is detected, is thereby kept high. The method for detecting a prospective abnormal pattern is proposed in U.S. Ser. No. 08/590,534.

Image signals have characteristics such that the signal value recognized from a prospective abnormal pattern may vary in accordance with the amount of change in the image signal corresponding to the areas surrounding the prospective abnormal pattern. FIGS. 11A and 11B are explanatory views showing signal values representing a prospective abnormal pattern, which is located at a flat portion. FIGS. 12A and 12B are explanatory views showing signal values representing a prospective abnormal pattern, which is located at a slant portion. For example, as illustrated in FIG. 11A, the signal value representing the prospective abnormal pattern located at a portion (herein referred to as the flat portion), at which the change in the signal value of the areas surrounding the prospective abnormal pattern is comparatively small, may have a level equal to h. In such cases, as illustrated in FIG. 11B, after the morphology operation processing is carried out on the image signal, the level h of the signal value representing the prospective abnormal pattern does not change. FIG. 12A shows the signal value representing the prospective abnormal pattern located at a portion (herein referred to as the slant portion), at which the change in the signal value of the areas surrounding the prospective abnormal pattern is large. In FIG. 12A, the signal value representing the prospective abnormal pattern has the same level as the level h of the signal value representing the prospective abnormal pattern located at the flat portion. However, in such cases, as illustrated in FIG. 12B, the signal value representing the prospective abnormal pattern located at the slant portion is recognized to be equal to a value H, which is smaller than the signal value h. As a result, the signal value of the image signal having been obtained from the morphology operation processing becomes equal to H, which is smaller than the signal value h. In particular, as the amount of change in the image signal corresponding to the areas surrounding the prospective abnormal pattern becomes large, the signal value recognized from the prospective abnormal pattern becomes small. In this manner, the signal value recognized from the prospective abnormal pattern varies in accordance with the amount of change in the image signal corresponding to the areas surrounding the prospective abnormal pattern. In such cases, if the threshold value, which is used in making a judgment as to whether the pattern is or is not the prospective abnormal pattern, is a fixed value, there will be the risk that a prospective abnormal pattern located at a portion, at which the amount of change in the image signal is comparatively large, cannot be detected, and an abnormal pattern is left unnoticed.

SUMMARY OF THE INVENTION

The primary object of the present invention is to provide a method for detecting a prospective abnormal pattern, wherein the performance for detecting an prospective abnormal pattern in accordance with an image signal, which represents a radiation image, is enhanced regardless of the amount of change in the signal value of the image signal.

Another object of the present invention is to provide a method for detecting a prospective abnormal pattern, which is suitable for use in a technique for computer aided diagnosis of a medical image.

The present invention provides a first method for detecting a prospective abnormal pattern, comprising the steps of:

exposing a stimulable phosphor sheet, on which a radiation image of an object has been stored, to stimulating rays, which cause the stimulable phosphor sheet to emit light in proportion to the amount of energy stored thereon during its exposure to radiation, detecting the emitted light by a photoelectric read-out means, an image signal representing the radiation image being thereby obtained, carrying out threshold value processing in accordance with the obtained image signal, and thereby detecting a prospective abnormal pattern from the radiation image, wherein the improvement comprises the step of setting a predetermined threshold value, which is used in the threshold value processing for detecting the prospective abnormal pattern, to be a small value as the amount of change in the image signal corresponding to the region in the vicinity of the prospective abnormal pattern becomes large.

The term "threshold value used in threshold value processing for detecting a prospective abnormal pattern" as used herein means the threshold value, which is used in making a judgment as to whether a pattern is or is not the prospective abnormal pattern. This also applies to the methods for detecting a prospective abnormal pattern in accordance with the present invention, which will be described later.

The present invention also provides a second method for detecting a prospective abnormal pattern, wherein the first method for detecting a prospective abnormal pattern in accordance with the present invention is modified such that the improvement may further comprise the steps of:

calculating a normalized read-out sensitivity and a normalized latitude in accordance with the image signal, the normalized read-out sensitivity and the normalized latitude being equivalent to read-out conditions, which are appropriate for obtaining a visible image reproduced from the radiation image, and setting the predetermined threshold value to be a large value as the normalized read-out sensitivity becomes large and/or as the normalized latitude becomes small.

The detection of the prospective abnormal pattern may be carried out with (1) a detection process using a morphology filter, comprising the steps of:

a) carrying out a morphology operation, in which an opening processing is carried out on a high luminance-high signal level type of original image signal by using a multi-scale and a multiply structure element, and an image signal having been obtained from the opening processing is subtracted from the original image signal, and b) comparing the value, which has been obtained from the morphology operation, and the predetermined threshold value with each other.

Alternatively, the detection of the prospective abnormal pattern may be carried out with (2) a detection process using a morphology filter, comprising the steps of:

a) carrying out a morphology operation, in which an opening processing is carried out on a high luminance-high signal level type of original image signal by using a multi-scale and a multiply structure element, and an image signal having been obtained from the opening processing is subtracted from the original image signal, a first value being obtained from the morphology operation, b) calculating a second value in accordance with differential information, which is obtained by subtracting a Minkowski difference of the image signal from a Minkowski sum of the image signal, c) comparing the first value and the corresponding predetermined threshold value with each other, d) comparing the second value and the corresponding predetermined threshold value with each other, and e) detecting the prospective abnormal pattern in accordance with the results of the two comparisons.

The detection process using the morphology filter, which is described in (1) above and in which the opening processing is carried out on the high luminance-high signal level type of the image signal, also includes a detection process using a morphology filter, in which closing processing is carried out on a high density-high signal level type of image signal. This is because the opening processing, which is carried out on the high luminance-high signal level type of the image signal, and the closing processing, which is carried out on the high density-high signal level type of the image signal, are substantially identical with each other, except that the image signal is taken as the density or is taken as the luminance.

The aforesaid threshold value in the second method for detecting a prospective abnormal pattern in accordance with the present invention should preferably be set such that it may be in inverse proportion to the normalized latitude. Alternatively, the aforesaid threshold value should preferably be set such that it may be in proportion to the square root of the normalized read-out sensitivity. As another alternative, the aforesaid threshold value should preferably be set such that it may be in inverse proportion to the normalized latitude and in proportion to the square root of the normalized read-out sensitivity.

The read-out sensitivity (S value) and the latitude (L value) in the second method for detecting a prospective abnormal pattern in accordance with the present invention will hereinbelow be described in detail.

In the CR, the "read-out sensitivity and contrast adjusting function utilizing the preliminary readout," which is referred to as the EDR, is employed. FIG. 7 is a flow chart showing the EDR processing. As illustrated in FIG. 7, an EDR image signal is obtained from the preliminary readout, which is carried out before the final readout and in which a stimulable phosphor sheet (hereinbelow often referred to as the imaging plate, i.e. IP) is coarsely scanned with a weak laser beam. Also, image recording menu information is inputted when an ID information for identifying the patient is registered. From the image signal and the image recording menu information, a subdivision pattern, in which the recording area on the stimulable phosphor sheet is divided into a plurality of subdivisions, is determined. Also, the shape and location of an irradiation field in each of the subdivisions are determined. Thereafter, a probability density function of the image signal (the image density), which corresponds to the region inside of the determined irradiation field, is formed. FIGS. 8A and 8B are graphs showing examples of probability density functions of image signals corresponding to regions inside of irradiation fields. As illustrated in FIGS. 8A and 8B, the probability density functions of the image signals have patterns inherent to the image recording menus. The image recording menu is determined by the portion of the object, the image of which is recorded, and the image recording method, such as simple image recording or contrasted image recording. By the utilization of such characteristics of the probability density function, the maximum value $S_1$ and the minimum value $S_2$ of the effective image signal can be detected. In this manner, the read-out conditions for the final readout can be adjusted such that the image density and the contrast may become appropriate.

The read-out conditions are specified by the two parameters, i.e., the read-out sensitivity (S value) and the latitude (L value) described above. Specifically, the read-out conditions determine the sensitivity of a photomultiplier and the gain of a multiplier. The final read-out image signal, which is obtained by carrying out the final readout under the adjusted read-out conditions, has been normalized to predetermined digital values regardless of the kind of the object and the kind of the image recording method used. Therefore, the image processing, which is carried out on the final read-out image signal, and the storage of the final read-out image signal can be carried out easily. Further, from the final read-out image signal, a visible image having an appropriate density or luminance and an appropriate contrast can be reproduced on photographic film, a CRT monitor, or the like.

FIG. 9 is a graph showing a principle, upon which the EDR processing is based.

With reference to FIG. 9, a first quadrant shows the relationship between the dose of X-rays irradiated to an IP and the intensity of light emitted by the IP. The intensity of the light emitted by the IP is in proportion to the dose of X-rays irradiated to the IP over a wide range of the dose. The relationship is one of the features of the IP which are worthy of special mention.

The second quadrant shows the EDR function, i.e., shows the relationship between the intensity of the emitted light, which is entered into a read-out means, and an output digital signal, which is obtained under the read-out conditions having been adjusted by the EDR.

The third quadrant shows how the image emphasis processing (i.e., frequency processing and gradation processing) is carried out for obtaining display characteristics appropriate for diagnostic purposes, or the like. In FIG. 9, an example of a gradation processing curve appropriate for a mamma image is shown.

The fourth quadrant shows a characteristic curve of an output photograph in the CR system. Specifically, the dose of X-rays irradiated to the IP is plotted on the horizontal axis, and the density on photographic film is plotted on the vertical axis extending downwardly. The characteristic curve takes on the form of an inverted characteristic curve of an X-ray photograph obtained with an ordinary fluorescent intensifying screen-film system. As described above, with the EDR, the maximum value $S_1$ and the minimum value $S_2$ of the image signal effective for diagnostic purposes, or the like, are detected from the probability density function of the EDR image signal. Also, the read-out conditions are adjusted such that the maximum value $S_1$ and the minimum value $S_1$ may be converted respectively into values $Q_1$ and $Q_2$, which have been set previously for each image recording menu.

Specifically, as for an example (i), in which the dose of X-rays irradiated to the IP is high and the image signal range is narrow, the EDR adjusts the read-out conditions as indicated by (A). As for an example (ii), in which the dose of X-rays irradiated to the IP is low and the image signal range is wide, the EDR adjusts the read-out conditions as indicated by (B). As a result, the characteristic curve of the CR system varies for different doses of X-rays and different widths of image signal ranges, and an appropriate image density and an appropriate contrast can be obtained in every case. This feature is markedly different from the characteristic curve of the conventional fluorescent intensifying screen-film system.

As described above, in the CR, the read-out conditions are defined by the two parameters, i.e., the read-out sensitivity and the latitude. FIG. 10 is a graph showing the relationship between the amount of light emitted by an IP and an output value, the graph serving as an aid in explaining a read-out sensitivity (S value) and a latitude (L value), which serve as read-out conditions. The S value is the index representing the read-out sensitivity, and the L value is the index representing the latitude. The read-out conditions, under which the image signal is obtained, can be known from the two indexes.

The S value, which is the index representing the read-out sensitivity, is defined by Formulas (12) and (13)

$$S=4\times10^{4-Sk} \tag{12}$$

$$Sk=\log(X/20(mR))+3.0 \tag{13}$$

wherein Sk is the value representing the amount of light emitted by the IP, which amount of light corresponds to the median value (511 in the cases of 10 bits) of the digital picture element values.

The value Sk representing the amount of light emitted by the IP is of the logarithmic scale, wherein the amount of emitted light, which is obtained from the IP having been exposed to a dose of 20mR (=5.16×10$^{-6}$ C/kg) at a tube voltage of 25 kVp of an Mo tube, is taken as a reference value of 3.0. In cases where the Sk value is equal to the reference value of 3.0, the S value is equal to 40. As the dose of X-rays irradiated to the IP becomes relatively large, the Sk value becomes large and the S value becomes small. This means that, since the amount of light emitted by the IP is large, even if the read-out sensitivity is low, a sufficient signal can be taken up.

The L value is the index representing the range of the amount of light emitted by the IP, which range has its center at the Sk value and is digitized. The L value is defined by Formula (14)

$$L=(1024/1)\times\{(\log S_1 - \log S_2)/(Q_1-Q_2)\} \quad (14)$$

wherein $S_1$ and $S_2$ represent the aforesaid characteristic values detected by the EDR, and $Q_1$ and $Q_2$ represent the picture element values corresponding respectively to the characteristic values $S_1$ and $S_2$.

For example, in cases where images having the same contrast of energy from X-rays are respectively read out with an L value of 1 and an L value of 2, the digital values obtained with the L value of 1 have a difference two times as large as the difference of the digital values obtained with the L value of 2.

With the EDR, the read-out conditions (i.e., the S value and the L value) are adjusted by primarily aiming at obtaining a reproduced visible image which has an appropriate density and an appropriate contrast and can serve as an effective tool in, particularly, the efficient and accurate diagnosis of an illness. For example, as for an image having a narrow dynamic range, the contrast of the image is positively enhanced such that a visible image having good image quality can be reproduced and used as an effective tool in, particularly, the accurately and efficient diagnosis of an illness.

The S value and the L value, which serve as the read-out conditions, are adjusted in the manner described above by the EDR.

A technique for adjusting an appropriate read-out sensitivity and an appropriate level of contrast with the EDR, wherein the aforesaid preliminary readout need not be carried out, has been proposed in, for example, U.S. Pat. No. 5,046,147. The EDR, wherein the preliminary readout need not be carried out, will be described hereinbelow.

In the aforesaid system utilizing the preliminary readout, the radiation image having been stored on the stimulable phosphor sheet is approximately ascertained by carrying out the preliminary readout. With the first method for detecting a prospective abnormal pattern in accordance with the present invention, the preliminary readout is not carried out, and the radiation image having been stored on the stimulable phosphor sheet cannot be approximately ascertained previously. Therefore, during the operation for reading out the radiation image from the stimulable phosphor sheet, the detection range for the detection of the light emitted by the stimulable phosphor sheet is set to be sufficiently wide. In this manner, the entire information of the radiation image can be detected as the image signal. In accordance with the detected image signal, in the same manner as that in the system utilizing the preliminary readout, calculations are made to find the two parameters, i.e., the read-out sensitivity (the S value) and the latitude (the L value), which serve as the read-out conditions for obtaining an appropriate reproduced visible image. Also, the image signal, which has been obtained from the image read-out operation, is converted in accordance with the calculated read-out sensitivity (S value) and the calculated latitude (L value).

During the conversion processing, a conversion table may be created in accordance with the calculated read-out sensitivity (S value) and the calculated latitude (L value). Also, the entire image signal may be converted in accordance with the conversion table.

Further, when the prospective abnormal pattern is to be detected from the image signal, which has been obtained from the conversion processing, by utilizing the aforesaid morphology filter, or the like, the predetermined threshold value to be used in detecting the prospective abnormal pattern may be changed in accordance with the read-out sensitivity and/or the latitude.

The present invention also provides a third method for detecting a prospective abnormal pattern, comprising the steps of:

carrying out a preliminary read-out operation by exposing a stimulable phosphor sheet, on which a radiation image of an object has been stored, to stimulating rays, which cause the stimulable phosphor sheet to emit light in proportion to the amount of energy stored thereon during its exposure to radiation and which have an energy level lower than the energy level of stimulating rays used in a final read-out operation, and detecting the emitted light by a photoelectric read-out means, an image signal representing the radiation image being thereby obtained, image information of the radiation image being approximately ascertained from the obtained image signal, adjusting a read-out sensitivity and a latitude, which serve as read-out conditions for the final read-out operation, in accordance with the information having been obtained from the preliminary read-out operation, carrying out the final read-out operation by exposing the stimulable phosphor sheet to the stimulating rays, and detecting the light, which is emitted by the stimulable phosphor sheet during its exposure to the stimulating rays, by a photoelectric read-out means, an image signal representing the radiation image being thereby obtained, the final read-out operation being carried out under the adjusted read-out conditions, carrying out threshold value processing in accordance with the image signal, which has been obtained from the final read-out operation, and thereby detecting a prospective abnormal pattern from the radiation image, wherein the improvement comprises the steps of:

setting a predetermined threshold value, which is used in the threshold value processing for detecting the prospective abnormal pattern, to be a large value as the read-out sensitivity becomes large and/or as the latitude becomes small, and setting the predetermined threshold value to be a small value as the amount of change in the image signal corresponding to the region in the vicinity of the prospective abnormal pattern becomes large.

In the third method for detecting a prospective abnormal pattern in accordance with the present invention, the detection of the prospective abnormal pattern should preferably be carried out with one of the aforesaid two detection processes using the morphology filter. Also, the threshold value described above should preferably be set such that it may be in inverse proportion to the latitude. Alternatively, the threshold value described above should preferably be set such that it may be in proportion to the square root of the read-out sensitivity. As another alternative, the threshold value described above should preferably be set such that it may be in inverse proportion to the latitude and in proportion to the square root of the read-out sensitivity.

The first, second, and third methods for detecting a prospective abnormal pattern in accordance with the present invention may be applied to the aforesaid apparatus for the computer aided diagnosis of medical images.

Specifically, in the apparatus for computer aided diagnosis of medical images, a marking may be put on the prospective tumor pattern having been detected with one of the methods for detecting a prospective abnormal pattern in accordance with the present invention. Alternatively, characteristics of the detected prospective tumor pattern may be quantitatively presented. As another alternative, the entire image may be displayed on a display device, such as a CRT display device, with a standard image size, and only the prospective tumor pattern may be displayed with an enlarged image size. In such cases, the methods for detecting a prospective abnormal pattern in accordance with the present invention become more useful for the person, who views the radiation image, to make a judgment.

The setting of the threshold value in accordance with the amount of change in the image signal should preferably be carried out in the manner described below. Specifically, the setting of the predetermined threshold value in accordance with the amount of change in the image signal, which corresponds to the region in the vicinity of the prospective abnormal pattern, should preferably be carried out by carrying out differentiation processing with respect to each picture element, which is among all of the picture elements constituting the given image, the degree of inclination being thereby calculated for each picture element, and setting the predetermined threshold value to be small as the degree of inclination becomes large.

With the methods for detecting a prospective abnormal pattern in accordance with the present invention, the threshold value, which is used in making an ultimate judgment as to whether the pattern is or is not the abnormal pattern, is varied such that the threshold value may be set to be a small value as the amount of change in the image signal, which corresponds to the region in the vicinity of the prospective abnormal pattern, becomes large. Therefore, even if the amount of change in the image signal is large and the signal value representing the prospective abnormal pattern is recognized to be a value, which is smaller than the actual signal value in the processing for detecting the prospective abnormal pattern, the threshold value can be varied in accordance with the amount of change in the image signal, and the prospective abnormal pattern can be detected regardless of the signal value recognized to be small. Accordingly, the performance for detecting the abnormal pattern can be kept high, and the problems can be prevented from occurring in that the prospective abnormal pattern cannot be detected due to the signal value recognized to be small.

BRIEF DESCRIPTION OF THE DRAWINGS

FIG. 9 is a graph showing a principle, upon which EDR processing is based, FIG. 10 is a graph showing the relationship between the amount of light emitted by an IP and an output value, the graph serving as an aid in explaining a read-out sensitivity (S value) and a latitude (L value), which serve as read-out conditions.

DESCRIPTION OF THE PREFERRED EMBODIMENTS

The present invention will hereinbelow be described in further detail with reference to the accompanying drawings.

Figure 1:
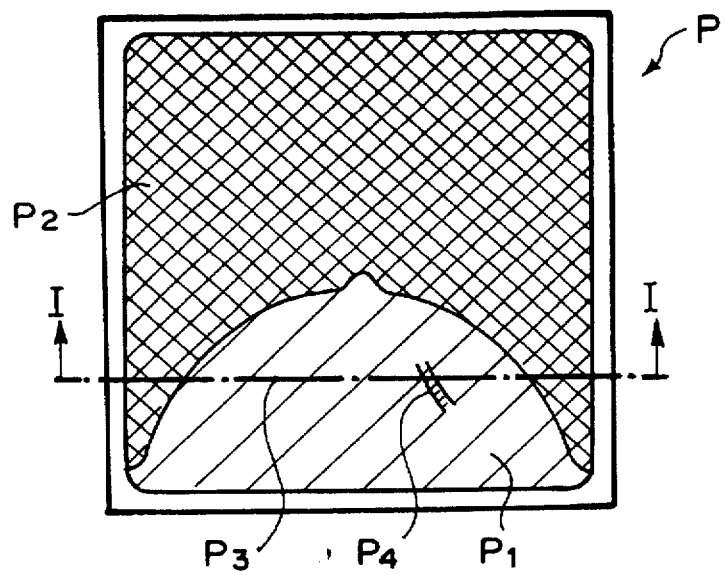
FIG. 1 is an explanatory view showing an X-ray image P containing an image $P_1$ of the mamma, which serves as an object.
Figure 2:
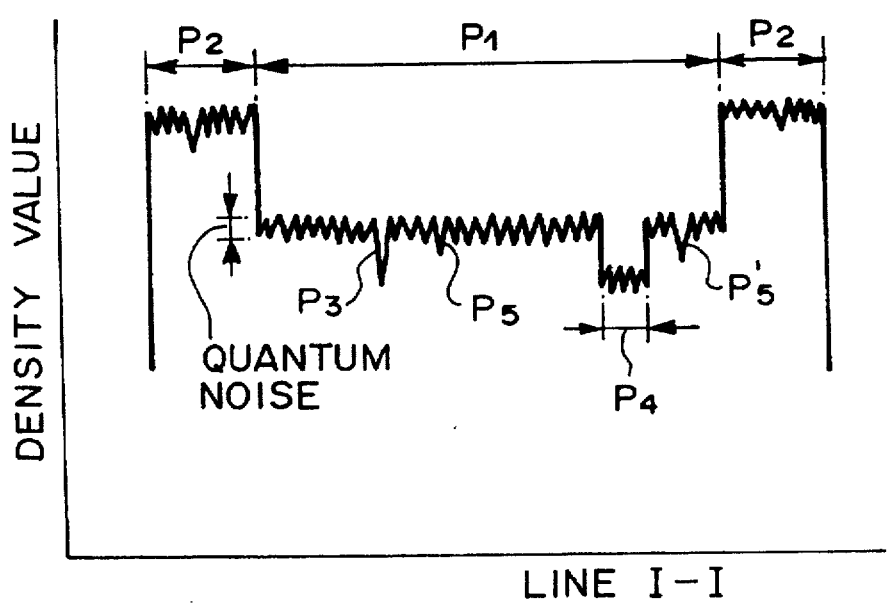
FIG. 2 is a graph showing a distribution of values of density (digital image signal) representing the X-ray image P, the distribution being taken along line I—I of FIG. 1, FIGS. 3A, 3B, and 3C are explanatory views showing how a threshold value is set.

FIG. 1 is an explanatory view showing an X-ray image P containing an image $P_1$ of the mamma, which serves as an object. FIG. 2 is a graph showing a distribution of values of density (digital image signal) representing the X-ray image P, the distribution being taken along line I—I of FIG. 1. In the X-ray image P, the region other than the mamma image $P_1$ is a background region $P_2$, upon which the X-rays impinged directly during an operation for recording the X-ray image P and which has the highest density in the X-ray image P.

In this embodiment, the image signal (the density value) is the high density-high digital value type of image signal, which has a high digital image value for a high density of the X-ray image P.

On the line I—I of FIG. 1, a small calcified pattern $P_3$ and a blood vessel pattern $P_4$ extending in a predetermined direction are located. Further, as illustrated in FIG. 2, quantum noise $P_5$ of the X-rays is contained in the entire image.

The processing with the morphology filter is carried out with Formula (7) on the image signal. In the morphology filter processing, structure elements, which are smaller than the blood vessel pattern $P_4$ and larger than the small calcified pattern $P_3$, are used. By the morphology filter processing, the blood vessel pattern $P_4$ is removed, and only the small calcified pattern $P_3$ is detected.

However, by the morphology filter processing, a portion $P_5'$ of the noise component $P_5$, or the like, which has the same size as the size of the small calcified pattern $P_3$, is detected together with the small calcified pattern $P_3$. Therefore, the portion $P_5'$ of the noise component, or the like, is removed by utilizing the differentiation information based upon the morphology operation carried out with Formula (9).

A large value of Mgrad of Formula (14) represents a high possibility that the pattern will be the small calcified pattern $P_3$. Therefore, a prospective calcified pattern Cs can be detected by making the calculation with Formula (10).

Figure 11A:
FIGS. 11A and 11B are explanatory views showing signal values representing a prospective abnormal pattern, which is located at a flat portion.
Figure 11B:
Figure 12A:
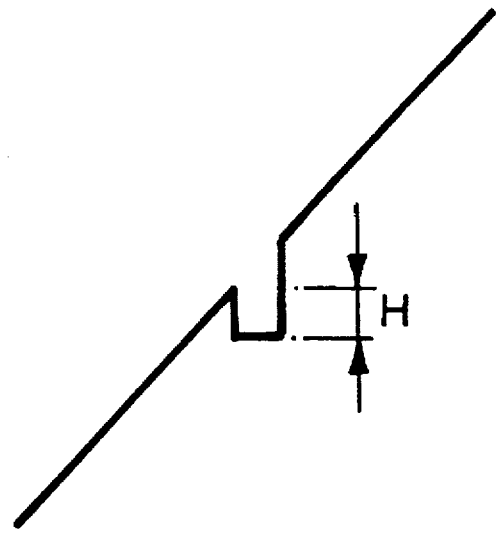
FIGS. 12A and 12B are explanatory views showing signal values representing a prospective abnormal pattern, which is located at a slant portion.
Figure 12B:
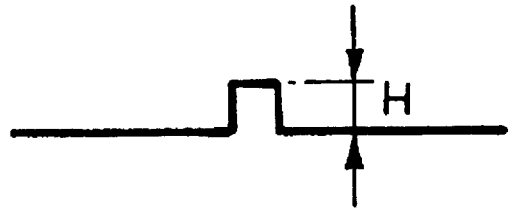

In Formula (10), T1 and T2 are the threshold values, which are used in discriminating the small calcified pattern $P_3$ and a non-calcified pattern (such as the portion $P_5'$ of the noise component) from each other. The threshold values T1 and T2 do not take the fixed values and are set in accordance with the amount of change in the image signal. Specifically, as illustrated in FIG. 2 and FIGS. 11A, 11B, the signal value representing the small calcified pattern $P_3$ serving as the prospective abnormal pattern located at the flat portion, at which the change in the signal value of the region in the vicinity of the prospective abnormal pattern is comparatively small, does not change after the morphology operation processing is carried out on the image signal. However, as illustrated in FIGS. 12A and 12B, as for the signal value representing the prospective abnormal pattern located at the slant portion, at which the change in the signal value of the region in the vicinity of the prospective abnormal pattern is large, even if the signal value representing the prospective abnormal pattern, which is located at the slant portion, has the same level as the level h of the signal value representing the prospective abnormal pattern, which is located at the flat portion, the signal value representing the prospective abnormal pattern located at the slant portion will be recognized to be equal to a value H, which is smaller than the signal value h. As a result, the signal value of the image signal having been obtained from the morphology operation processing becomes equal to H, which is smaller than the signal value h. In particular, as the amount of change in the image signal corresponding to the region in the vicinity of the prospective abnormal pattern becomes large, the signal value recognized from the prospective abnormal pattern becomes small. In this manner, the signal value recognized from the prospective abnormal pattern varies in accordance with the amount of change in the image signal corresponding to the region in the vicinity of the prospective abnormal pattern. In such cases, if the threshold value, which is used in making a judgment as to whether the pattern is or is not the prospective abnormal pattern, is a fixed value, there will be the risk that a prospective abnormal pattern located at a portion, at which the amount of change in the image signal is comparatively large, cannot be detected.

Therefore, in this embodiment, the threshold values are set in the manner described below in accordance with the amount of change in the image signal.

Figure 3A:
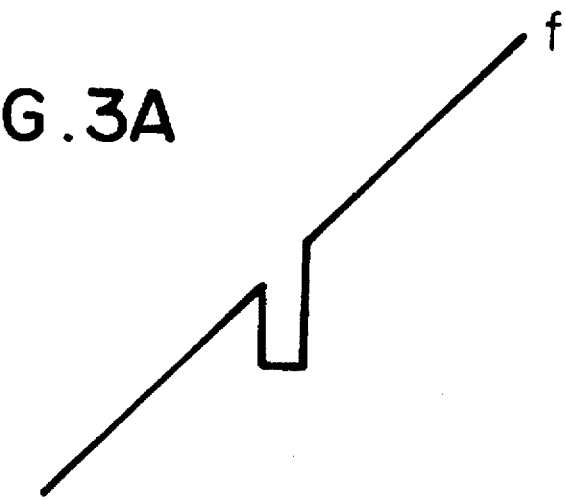

Firstly, a closing processing based upon a multiply structure element is carried out with Formula (15) shown below on an image signal f, which has a pattern shown in FIG. 3A, and a morphology signal f' is thereby obtained.

$$f' = \max \{(f \oplus Bi) \ominus Bi\} \tag{15}$$

Figure 3B:
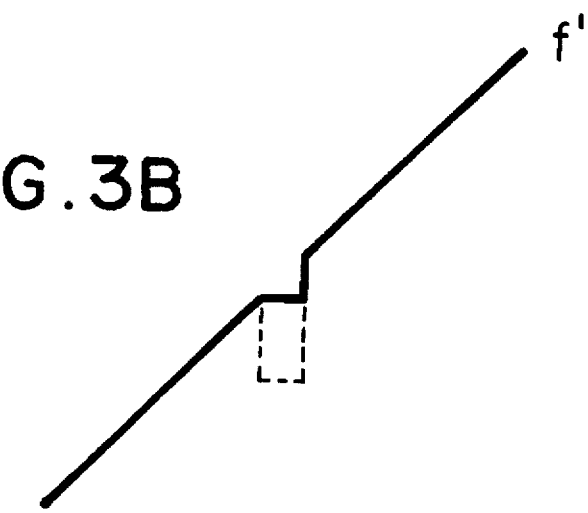
Figure 3C:
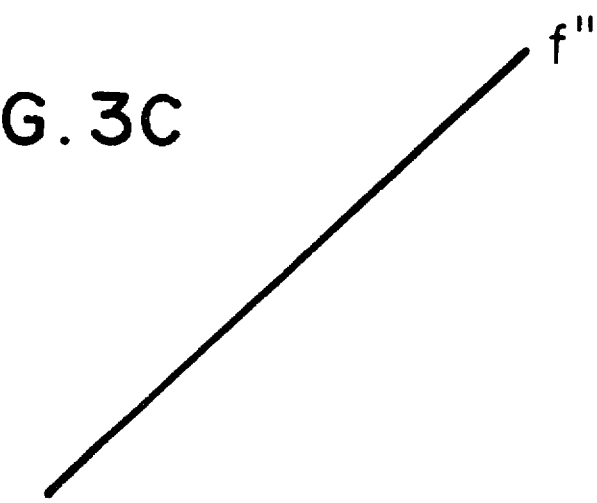
Figure 4:
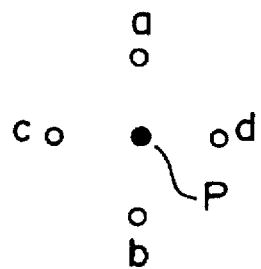
FIG. 4 is an explanatory view showing a differentiation processing for setting a threshold value.
Figure 6:
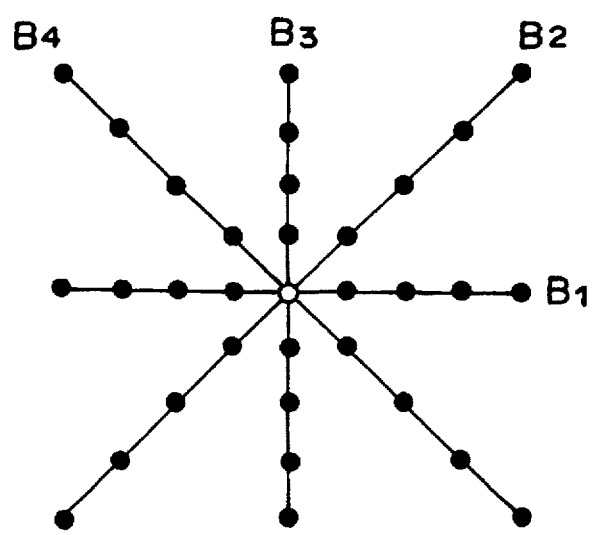
FIG. 6 is an explanatory view showing four structure elements employed in a morphology filter.
Figure 5A:
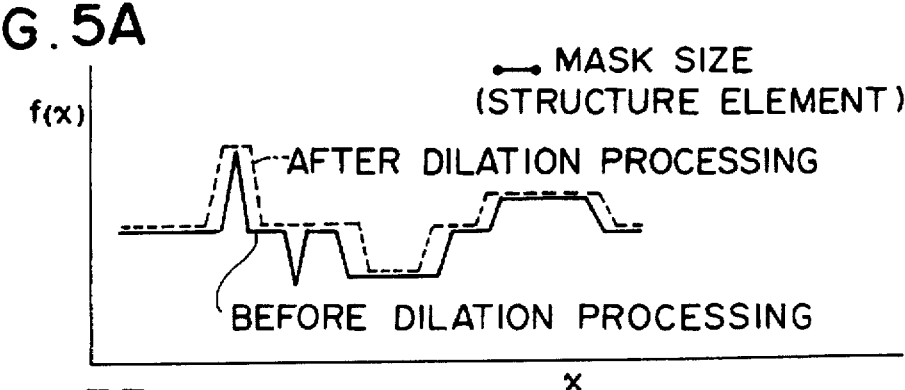
FIG. 5A is a graph showing how a dilation processing, which is one of fundamental operations with a morphology filter, is carried out.
Figure 5B:
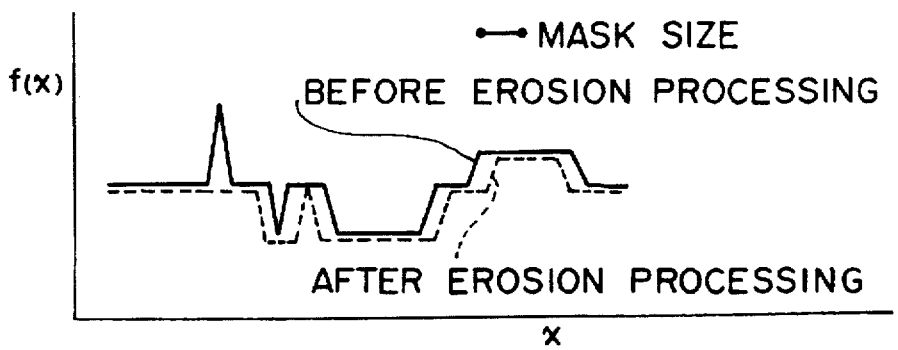
FIG. 5B is a graph showing how an erosion processing, which is one of fundamental operations with a morphology filter, is carried out.
Figure 5C:
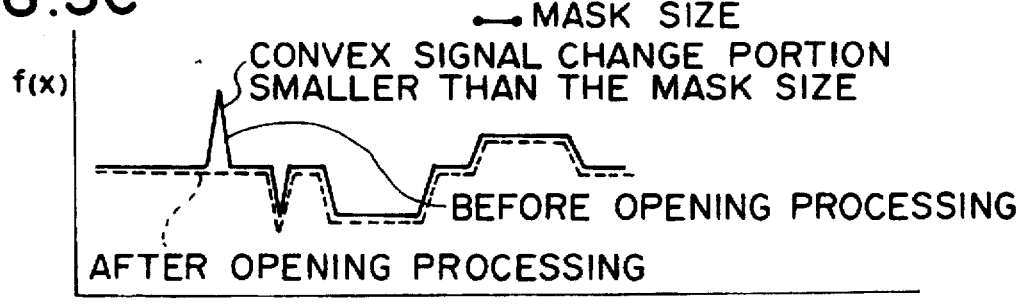
FIG. 5C is a graph showing how an opening processing, which is one of fundamental operations with a morphology filter, is carried out.
Figure 5D:
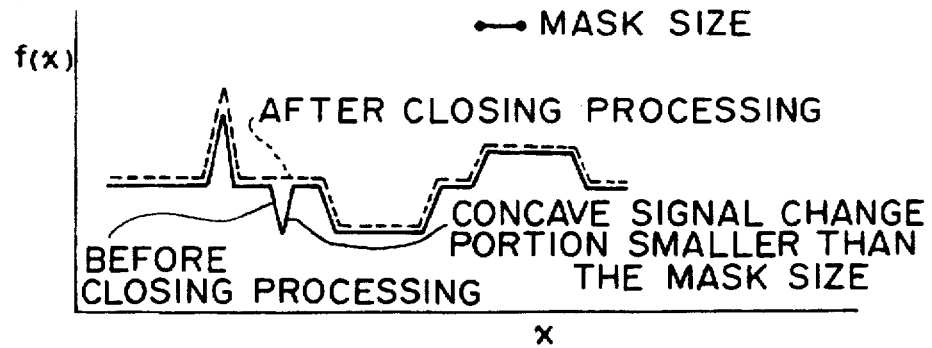
FIG. 5D is a graph showing how a closing processing, which is one of fundamental operations with a morphology filter, is carried out.
Figure 7:
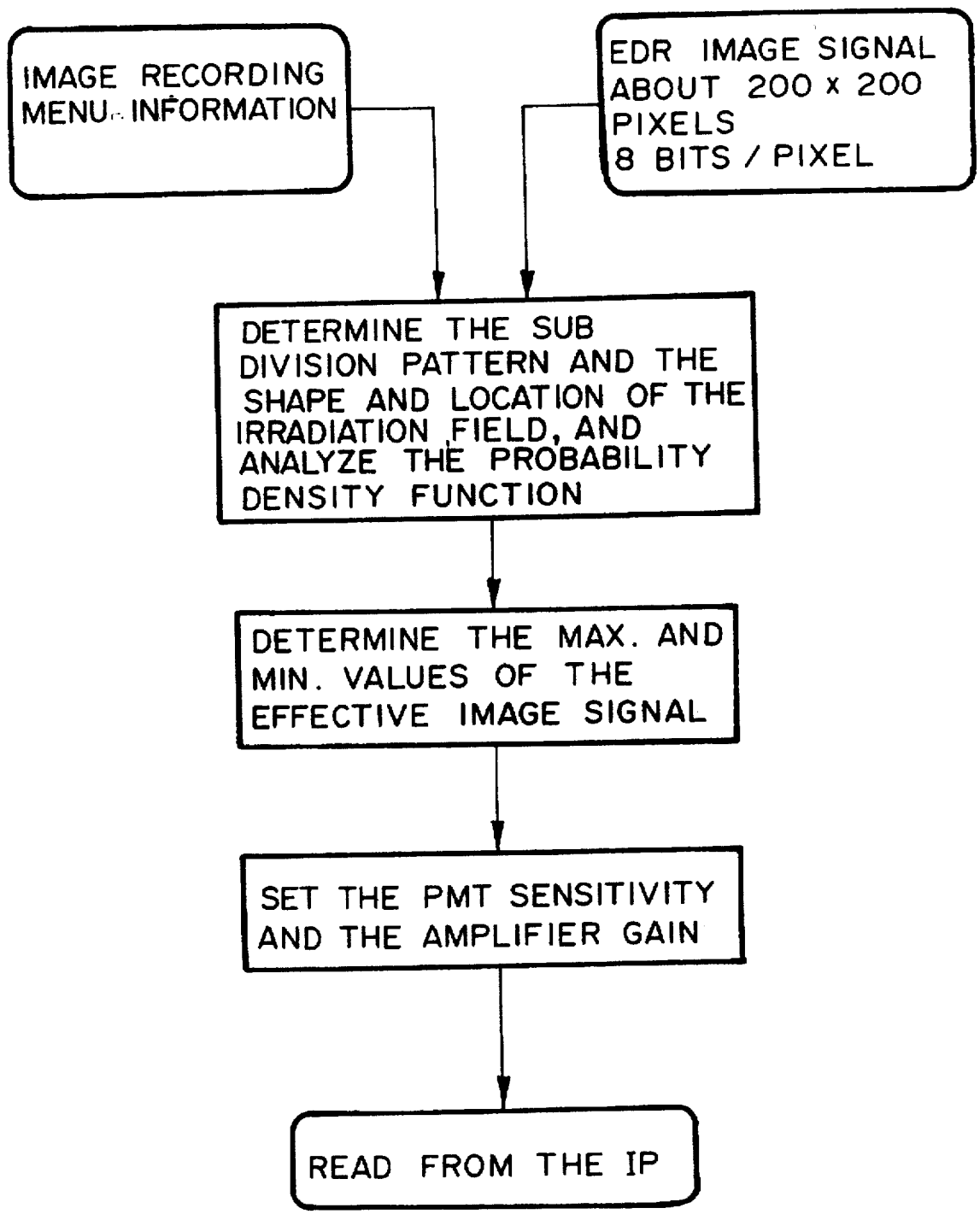
FIG. 7 is a flow chart showing EDR processing.
Figure 8A:
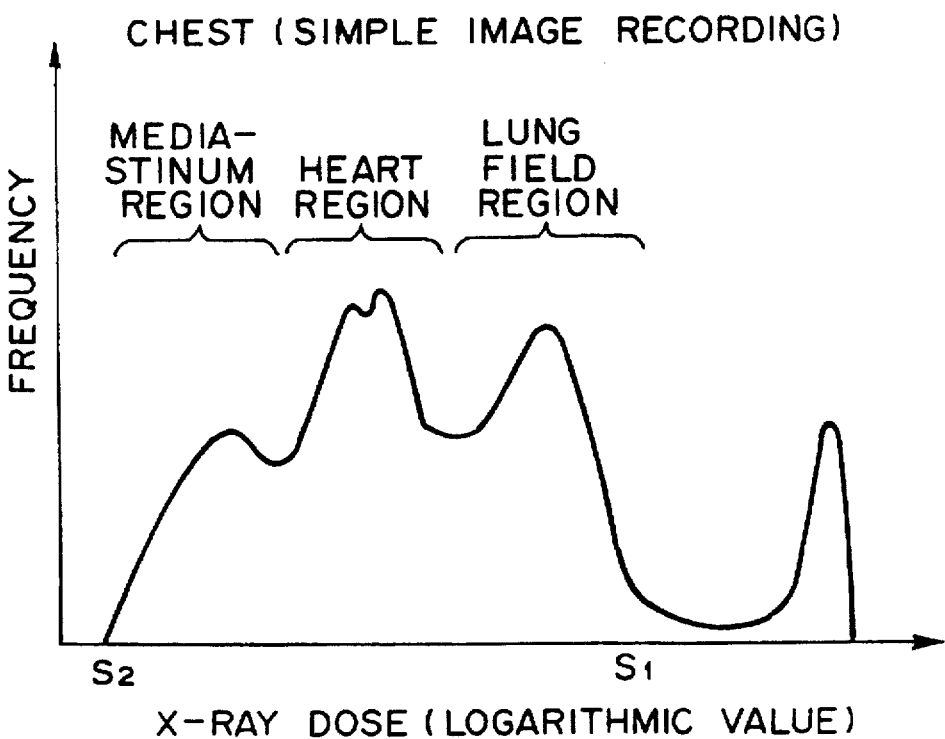
FIGS. 8A and 8B are graphs showing examples of probability density functions of image signals corresponding to regions inside of irradiation fields.
Figure 8B:
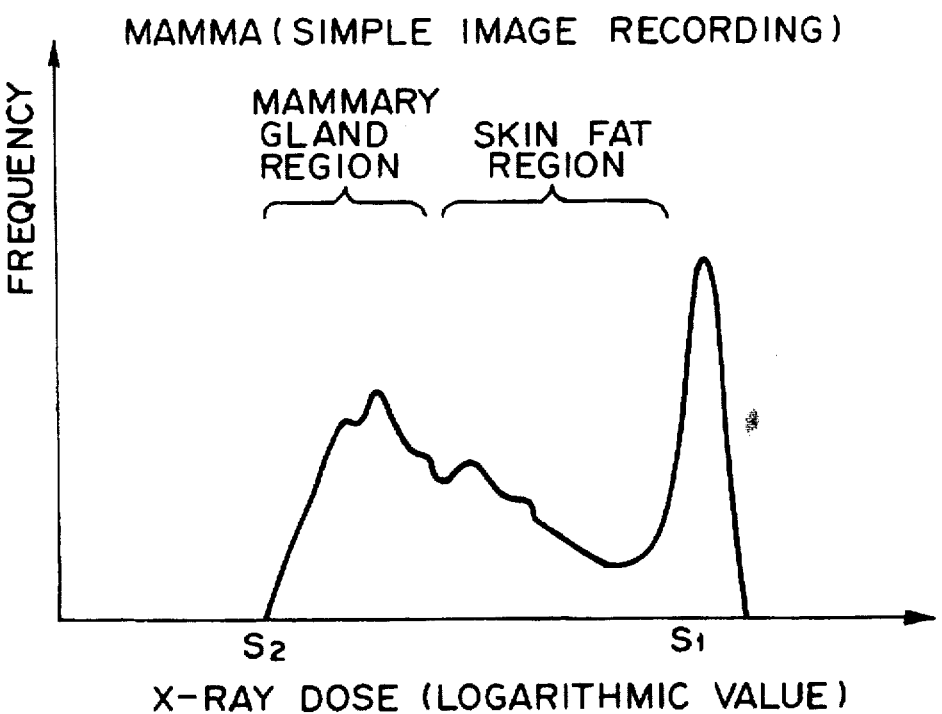

The morphology signal f' obtained from the closing processing has the signal value distribution shown in FIG. 3B. Thereafter, a filtering processing is carried out on the morphology signal f' by using a mask having a size of 15×15. The morphology signal f' is thus blurred, and a morphology signal f" shown in FIG. 3C is thereby obtained. A simple differentiation processing is then carried out on the thus obtained morphology signal f". As illustrated in FIG. 4, the simple differentiation processing is carried out by calculating a differential value D at a picture element of interest P, which is subjected to the differentiation processing. The calculation is carried out with Formula (16) shown below with respect to four picture elements a, b, c, and d, which are located in the vicinity of the picture element of interest P.

$$D = |a-b| + |c-d| \tag{16}$$

The differential value D having thus been calculated represents the degree of inclination of the image signal f at the picture element of interest P.

Thereafter, a correction value $\alpha$ is calculated with Formula (17) shown below. The correction value $\alpha$ is used for correcting the predetermined threshold value T.

$$\alpha = D/2 \tag{17}$$

wherein if $\alpha > 4$, then $\alpha = 4$.

The predetermined threshold value is then corrected with the correction value $\alpha$. The correction is carried out with Formula (18), and threshold values T1' and T2' are thereby obtained.

$$T1' = T1 - \alpha$$

$$T2' = T2 - \alpha \tag{18}$$

The threshold values T1' and T2' are thus set. In this manner, even if the amount of change in the image signal corresponding to the region in the vicinity of the prospective abnormal pattern (in this case, the small calcified pattern $P_3$) is large and the signal value representing the prospective abnormal pattern, which signal value is obtained after the morphology processing, becomes smaller than the actual signal value, the problems can be prevented from occurring in that the small calcified pattern $P_3$ cannot be detected. Thus the small calcified pattern $P_3$ can be detected accurately.

Alternatively, the correction value $\alpha$ may be added to the morphology signal f', which has been obtained with Formula (15) shown above, and a morphology signal (f'+$\alpha$) may thereby be obtained. The processing with Formula (7) or (8) shown above may then be carried out in accordance with the morphology signal (f'+$\alpha$).

In the embodiment described above, the morphology filter is employed for the detection of the prospective abnormal pattern. However, the method for detecting a prospective abnormal pattern in accordance with the present invention is not limited to the use of the morphology filter and is also applicable to any of the other techniques, with which the prospective abnormal pattern can be detected by using a threshold value.

Also, the method for detecting a prospective abnormal pattern in accordance with the present invention may be applied to the aforesaid apparatus for computer aided diagnosis of medical images.

Further, the threshold values may also be set in accordance with the read-out sensitivity (the S value) and the latitude (the L value), which have been obtained from the EDR processing.

Specifically, the level of the noise component $P_5$ fluctuates in accordance with the S value and the L value, which are obtained from the EDR processing. Therefore, if the threshold values are set to be the fixed values, the abnormal pattern cannot be detected accurately. In such cases, the threshold values T1 and T2 are set respectively with Formulas (19) and (20) by using the L value, which is obtained from the EDR processing.

$$T1 = C_1/L \quad (C_1 \text{ is a fixed number}) \quad (19)$$

$$T2 = C_2/L \quad (C_2 \text{ is a fixed number}) \quad (20)$$

More specifically, as described above, in cases where the L value obtained from the EDR processing is large, the width of the obtained image signal values becomes small, and therefore the contrast of the portion $P_5'$ of the noise component is also reduced. Accordingly, even if the threshold values are set as being small values, the small calcified pattern $P_3$ and the portion $P_5'$ of the noise component, which is a non-calcified pattern, can be discriminated from each other. In this manner, only the small calcified pattern $P_3$ can be detected accurately.

In cases where the L value obtained from the EDR processing is small, the width of the obtained image signal values becomes large, and therefore the contrast of the portion $P_5'$ of the noise component is also increased. In such cases, if the threshold values are fixed as in the conventional techniques, the small calcified pattern $P_3$ and the portion $P_5'$ of the noise component, which is a non-calcified pattern, cannot be discriminated from each other. However, with this embodiment of the method for detecting a prospective abnormal pattern in accordance with the present invention, wherein the threshold values are set to be large when the L value becomes small, the small calcified pattern $P_3$ and the portion $P_5'$ of the noise component, which is a non-calcified pattern, can be discriminated from each other.

Alternatively, the threshold values T1 and T2 may be set respectively with Formulas (21) and (22) by using the S value, which is obtained from the EDR processing, such that they may be in proportion to the square root of the S value. As another alternative, the threshold values T1 and T2 may be set respectively with Formulas (23) and (24) such that they may be in inverse proportion to the L value and in proportion to the square root of the S value.

$$T1 = C_3 S^{1/2} \quad (C_3 \text{ is a fixed number}) \quad (21)$$

$$T2 = C_4 S^{1/2} \quad (C_4 \text{ is a fixed number}) \quad (22)$$

$$T1 = C_5 S^{1/2}/L \quad (C_5 \text{ is a fixed number}) \quad (23)$$

$$T2 = C_6 S^{1/2}/L \quad (C_6 \text{ is a fixed number}) \quad (24)$$

As described above, in cases where the threshold values are set in accordance with the S value and/or the L value having been obtained from the EDR processing, the performance, with which the abnormal pattern is detected, can be kept high regardless of the read-out conditions, under which the image signal is detected and which are adjusted with the EDR.

The setting of the threshold values in accordance with the S value and/or the L value having been obtained from the EDR processing may thus be carried out in cases where the morphology filter is utilized and in cases where the other techniques, with which the prospective abnormal pattern can be detected by using a threshold value T, are utilized.

In such cases, in the same manner as that represented by Formulas (21) and (22), the threshold value T may be set such that it may be in proportion to the square root of the S value having been obtained from the EDR processing. Alternatively, in the same manner as that represented by Formulas (23) and (24), the threshold value T may be set such that it may be in inverse proportion to the L value and in proportion to the square root of the S value.

What is claimed is:

1. A method for detecting a prospective abnormal pattern, comprising the steps of:

exposing a stimulable phosphor sheet, on which a radiation image of an object has been stored, to stimulating rays, which cause the stimulable phosphor sheet to emit light in proportion to the amount of energy stored thereon during its exposure to radiation, detecting the emitted light by a photoelectric read-out means, an image signal representing the radiation image being thereby obtained, carrying out threshold value processing in accordance with the obtained image signal, and thereby detecting a prospective abnormal pattern from the radiation image, wherein the improvement comprises the step of setting a predetermined threshold value, which is used in the threshold value processing for detecting the prospective abnormal pattern, to be a small value as the amount of change in the image signal corresponding to the region in the vicinity of the prospective abnormal pattern becomes large.

2. A method as defined in claim 1 wherein the improvement further comprises the steps of:

calculating a normalized read-out sensitivity and a normalized latitude in accordance with the image signal, said normalized read-out sensitivity and said normalized latitude being equivalent to read-out conditions, which are appropriate for obtaining a visible image reproduced from the radiation image, and setting said predetermined threshold value to be a large value as said normalized read-out sensitivity becomes large and/or as said normalized latitude becomes small.

3. A method as defined in claim 1 wherein the detection of the prospective abnormal pattern is carried out with a detection process using a morphology filter, comprising the steps of:

a) carrying out a morphology operation, in which an opening processing is carried out on a high luminance-high signal level type of original image signal by using a multi-scale and a multiply structure element, and an image signal having been obtained from the opening processing is subtracted from the original image signal, and b) comparing the value, which has been obtained from the morphology operation, and said predetermined threshold value with each other.

4. A method as defined in claim 2 wherein the detection of the prospective abnormal pattern is carried out with a detection process using a morphology filter, comprising the steps of:

a) carrying out a morphology operation, in which an opening processing is carried out on a high luminance-high signal level type of original image signal by using a multi-scale and a multiply structure element, and an image signal having been obtained from the opening processing is subtracted from the original image signal, and b) comparing the value, which has been obtained from the morphology operation, and said predetermined threshold value with each other.

5. A method as defined in claim 1 wherein the detection of the prospective abnormal pattern is carried out with a detection process using a morphology filter, comprising the steps of:

a) carrying out a morphology operation, in which an opening processing is carried out on a high luminance-high signal level type of original image signal by using a multi-scale and a multiply structure element, and an image signal having been obtained from the opening processing is subtracted from the original image signal, a first value being obtained from the morphology operation, b) calculating a second value in accordance with differential information, which is obtained by subtracting a Minkowski difference of the image signal from a Minkowski sum of the image signal, c) comparing said first value and the corresponding predetermined threshold value with each other, d) comparing said second value and the corresponding predetermined threshold value with each other, and e) detecting the prospective abnormal pattern in accordance with the results of the two comparisons.

6. A method as defined in claim 2 wherein the detection of the prospective abnormal pattern is carried out with a detection process using a morphology filter, comprising the steps of:

a) carrying out a morphology operation, in which an opening processing is carried out on a high luminance-high signal level type of original image signal by using a multi-scale and a multiply structure element, and an image signal having been obtained from the opening processing is subtracted from the original image signal, a first value being obtained from the morphology operation, b) calculating a second value in accordance with differential information, which is obtained by subtracting a Minkowski difference of the image signal from a Minkowski sum of the image signal, c) comparing said first value and the corresponding predetermined threshold value with each other, d) comparing said second value and the corresponding predetermined threshold value with each other, and e) detecting the prospective abnormal pattern in accordance with the results of the two comparisons.

7. A method as defined in claim 2 wherein said predetermined threshold value is set such that it may be in inverse proportion to said normalized latitude and/or in proportion to the square root of said normalized read-out sensitivity.

8. A method as defined in claim 4 wherein said predetermined threshold value is set such that it may be in inverse proportion to said normalized latitude and/or in proportion to the square root of said normalized read-out sensitivity.

9. A method as defined in claim 6 wherein said predetermined threshold value is set such that it may be in inverse proportion to said normalized latitude and/or in proportion to the square root of said normalized read-out sensitivity.

10. A method as defined in claim 1 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

11. A method as defined in claim 2 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

12. A method as defined in claim 3 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

13. A method as defined in claim 4 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

14. A method as defined in claim 5 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

15. A method as defined in claim 6 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

16. A method as defined in claim 7 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

17. A method as defined in claim 8 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

18. A method as defined in claim 9 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

19. A method for detecting a prospective abnormal pattern, comprising the steps of:

carrying out a preliminary read-out operation by exposing a stimulable phosphor sheet, on which a radiation image of an object has been stored, to stimulating rays, which cause the stimulable phosphor sheet to emit light in proportion to the amount of energy stored thereon during its exposure to radiation and which have an energy level lower than the energy level of stimulating rays used in a final read-out operation, and detecting the emitted light by a photoelectric read-out means, an image signal representing the radiation image being thereby obtained, image information of the radiation image being approximately ascertained from the obtained image signal, adjusting a read-out sensitivity and a latitude, which serve as read-out conditions for the final read-out operation, in accordance with the information having been obtained from the preliminary read-out operation, carrying out the final read-out operation by exposing the stimulable phosphor sheet to the stimulating rays, and detecting the light, which is emitted by the stimulable phosphor sheet during its exposure to the stimulating rays, by a photoelectric read-out means, an image signal representing the radiation image being thereby obtained, the final read-out operation being carried out under the adjusted read-out conditions, carrying out threshold value processing in accordance with the image signal, which has been obtained from the final read-out operation, and thereby detecting a prospective abnormal pattern from the radiation image, wherein the improvement comprises the steps of:

setting a predetermined threshold value, which is used in the threshold value processing for detecting the prospective abnormal pattern, to be a large value as the read-out sensitivity becomes large and/or as the latitude becomes small, and setting said predetermined threshold value to be a small value as the amount of change in the image signal corresponding to the region in the vicinity of the prospective abnormal pattern becomes large.

20. A method as defined in claim 19 wherein the detection of the prospective abnormal pattern is carried out with a detection process using a morphology filter, comprising the steps of:

a) carrying out a morphology operation, in which an opening processing is carried out on a high luminance-high signal level type of original image signal by using a multi-scale and a multiply structure element, and an image signal having been obtained from the opening processing is subtracted from the original image signal, and b) comparing the value, which has been obtained from the morphology operation, and said predetermined threshold value with each other.

21. A method as defined in claim 19 wherein the detection of the prospective abnormal pattern is carried out with a detection process using a morphology filter, comprising the steps of:

a) carrying out a morphology operation, in which an opening processing is carried out on a high luminance-high signal level type of original image signal by using a multi-scale and a multiply structure element, and an image signal having been obtained from the opening processing is subtracted from the original image signal, a first value being obtained from the morphology operation, b) calculating a second value in accordance with differential information, which is obtained by subtracting a Minkowski difference of the image signal from a Minkowski sum of the image signal, c) comparing said first value and the corresponding predetermined threshold value with each other, d) comparing said second value and the corresponding predetermined threshold value with each other, and e) detecting the prospective abnormal pattern in accordance with the results of the two comparisons.

22. A method as defined in claim 19 wherein said predetermined threshold value is set such that it may be in inverse proportion to said latitude and/or in proportion to the square root of said read-out sensitivity.

23. A method as defined in claim 20 wherein said predetermined threshold value is set such that it may be in inverse proportion to said latitude and/or in proportion to the square root of said read-out sensitivity.

24. A method as defined in claim 21 wherein said predetermined threshold value is set such that it may be in inverse proportion to said latitude and/or in proportion to the square root of said read-out sensitivity.

25. A method as defined in claim 19 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

26. A method as defined in claim 20 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

27. A method as defined in claim 21 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

28. A method as defined in claim 22 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

29. A method as defined in claim 23 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

30. A method as defined in claim 24 wherein the setting of said predetermined threshold value in accordance with the amount of change in the image signal corresponding to the region in the vicinity of the prospective abnormal pattern is carried out by carrying out differentiation processing with respect to each picture element, which is among all of the picture elements constituting the given image, the degree of inclination being thereby calculated for each picture element, and setting said predetermined threshold value to be small as said degree of inclination becomes large.

* * * * *